(12) United States Patent
Gordon et al.

(10) Patent No.: US 7,202,198 B2
(45) Date of Patent: Apr. 10, 2007

(54) SUBSTITUTED PHENOLIC COMPOSITION AND PROCESS FOR USING SAME FOR INHIBITING MALODOURS

(75) Inventors: Mary E. Gordon, Belford, NJ (US); Charles E. J. Beck, Summit, NJ (US); Richard M. Boden, Ocean, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 358 days.

(21) Appl. No.: 10/458,517

(22) Filed: Jun. 10, 2003

(65) Prior Publication Data

US 2004/0253199 A1    Dec. 16, 2004

(51) Int. Cl.
A61K 8/00 (2006.01)
A61K 7/32 (2006.01)
A61K 7/00 (2006.01)
A01N 25/00 (2006.01)

(52) U.S. Cl. .................. 510/131; 424/65; 424/401; 424/405

(58) Field of Classification Search .............. 514/65; 424/65, 401, 405; 252/86–89; 510/131
See application file for complete search history.

(56) References Cited

U.S. PATENT DOCUMENTS

| | | | |
|---|---|---|---|
| 3,634,947 A | 1/1972 | Furgal | |
| 3,676,199 A | 7/1972 | Hewitt et al. | |
| 3,984,535 A | 10/1976 | Ghilardi et al. | |
| 5,158,992 A | 10/1992 | Caselli et al. | |
| 5,405,917 A | 4/1995 | Mueller, Jr. et al. | |
| 5,445,747 A * | 8/1995 | Kvietok et al. | 510/101 |
| 5,910,527 A | 6/1999 | Alper et al. | |
| 5,945,026 A | 8/1999 | Thames | |
| 6,133,226 A | 10/2000 | Knowlton et al. | |
| 6,139,775 A | 10/2000 | Thames | |
| 6,235,705 B1 | 5/2001 | Zembrodt et al. | |
| 6,436,894 B2 | 8/2002 | Zembrodt et al. | |
| 6,451,065 B2 | 9/2002 | Trinh et al. | |
| 6,503,489 B1 | 1/2003 | Wilson et al. | |
| 6,503,490 B2 * | 1/2003 | Johnson et al. | 424/65 |
| 6,514,489 B1 | 2/2003 | Shacknai et al. | |
| 6,528,013 B1 | 3/2003 | Trinh et al. | |
| 6,540,988 B1 | 4/2003 | Behan et al. | |
| 6,555,092 B2 | 4/2003 | Sembo et al. | |
| 6,558,680 B1 | 5/2003 | Riedel et al. | |
| 2001/0031280 A1 | 10/2001 | Ferrari et al. | |
| 2002/0065249 A1 | 5/2002 | Johnson et al. | |
| 2003/0069164 A1 | 4/2003 | Levinson et al. | |

FOREIGN PATENT DOCUMENTS

| | | |
|---|---|---|
| EP | 0 750 903 A1 | 1/1997 |
| EP | 0 979 644 | 2/2000 |
| GB | 1517042 | 7/1978 |
| WO | WO 00 25731 | 5/2000 |

OTHER PUBLICATIONS

Chemistry of Heterocyclic Compounds in Flavours and Aromas, G. Vernin, Published by Ellis Horwood, Ltd., 1982, pp. 54-56 and 65-67.

* cited by examiner

*Primary Examiner*—Douglas McGinty
*Assistant Examiner*—Preeti Kumar
(74) *Attorney, Agent, or Firm*—Elizabeth M Quirk; Joseph F. Leightner

(57) ABSTRACT

Described is a process for reducing a malodour formed as a result of fatty acid derivative degradation and/or organic amine degradation taking place in a fabric care base contained in a fabric article or in a cosmetic or therapeutic base adsorbed on the human epidermis by treating the base-bearing fabric article or base-bearing human epidermis with a synergistic mixture of t-butyl phenolic compounds which may also include at least one malodour-reducing fragrance component compatible with each of the phenolic composition components. Also described are novel compositions useful in carrying out the aforementioned process.

3 Claims, No Drawings

SUBSTITUTED PHENOLIC COMPOSITION AND PROCESS FOR USING SAME FOR INHIBITING MALODOURS

FIELD OF THE INVENTION

Reduction of a malodour formed as a result of fatty acid degradation and/or organic amine degradation taking place (a) in a fabric article having absorbed therein or adsorbed thereon a fabric care base or (b) on the human epidermis having adsorbed thereon a cosmetic or therapeutic base, each of which base contains one or more fatty acid derivatives and/or one or more amine derivatives, by treating the base-bearing fabric article or the base-bearing human epidermis with a synergistic mixture of t-butyl phenolic compounds optionally also including one or more fatty acid or amine degradation-caused malodour-reducing compatible fragrance compositions in synergistic combination therewith.

BACKGROUND OF THE INVENTION

Undesirable malodours are generated resulting from degradation, including biodegradation of organic amines and/or fatty acid derivatives contained in (a) fabric care bases (such as anti-static bases or anti-wrinkle bases) which are further absorbed in or adsorbed on clothing articles which are in direct contact with the human epidermis and (b) cosmetic and therapeutic bases which are further adsorbed on the human epidermis. Specifically, the action of human sweat, containing microorganisms belonging to the skin flora acts upon organic amines and/or fatty acid derivatives contained in compositions (also referred to herein as bases) which are absorbed in or adsorbed (a) on fabric articles such as clothing, whereby malodours are generated and are evolved into the environment adjacent to and circumscribing the wearer of the clothing or (b) on the human epidermis whereby malodours are generated and are evolved into the environment adjacent to and surrounding the cosmetic or therapeutic base-bearing human epidermis. The biodegradability of such organic amines is disclosed in U.S. Pat. Nos. 5,945,026 and 6,139,775.

The degradability of fatty acid derivatives is well documented in the literature, e.g. "Chemistry of Heterocyclic Compounds in Flavours and Aromas", G. Vernin, Published by Ellis Horwood, Ltd., 1982, pp. 54–56 and 65–67.

The prior art such as European Published Patent Application 0 750 903 A1 contains teachings of deodorant compositions which are suitable for preventing or curbing the development of malodour as a consequence of the conversion of components of perspiration moisture by organisms. The prior art such as United Kingdom Patent Specification 1,517,042 discloses the utilization of non-detergent materials, such as ethylenediamine tetraacetic acid for inhibiting the formation of fatty acids resulting from the degradation of skin secretions by *corynebacterium* while maintaining the viability of the *corynebacterium*.

Furthermore, U.S. Pat. No. 6,503,489 discloses a method for reducing or preventing body malodour by topically applying to human skin a perfume composition preferably capable of inhibiting lysozymes and also capable of selectively increasing the population of naturally-occurring deodorizing microorganisms on the surface of the skin. U.S. Pat. No. 6,503,490 discloses the achievement of a deodorancy benefit upon the human body or articles worn in close proximity thereto by application of a phenolic or enolic product that can be an anti-oxidant comprising a t-butyl phenol group such as BHT (2,6-di-t-butyl-4-methyl phenol) or TINOGARD TT (pentaerythritol tetrakis(3 -(3,5 -di-t-butyl-4-hydroxyphenyl)propionate)) (Ciba Specialty Chemical Corp. of Tarrytown, N.Y.). In addition, U.S. Pat. No. 6,540,988 discloses a method of reducing or preventing body malodour by topically applying to human skin perfume components, including benzyl salicylate and tetrahydrolinalool, indicated to be capable of inhibiting production of odoriferous steroids by micro-organisms on the skin.

However, nothing in the prior art discloses or suggests the enablement of the inhibition and reduction of malodours which are generated as a result of fatty acid and/or organic amine degradation taking place (a) on a fabric article such as clothing which fabric article is in direct contact with the human epidermis, where the fabric article has absorbed therein or adsorbed thereon a base, such as an anti-static base or an anti-wrinkle base which base includes a degradable organic amine and/or a degradable fatty acid derivative or (b) on the human epidermis, where the epidermis has adsorbed thereon a therapeutic or cosmetic base which base includes a degradable organic amine and/or a degradable fatty acid derivative. In addition, nothing in the prior discloses or suggests the unexpected advantage of employing the synergistic mixture of the t-butyl-substituted phenolic compounds, BHT and TINOGARD taken as a combination alone or taken further together with one or more malodour-inhibiting fragrances for inhibiting a malodour which is generated as a result of fatty acid and/or organic amine degradation taking place in (a) a fabric care base absorbed in or adsorbed on a fabric article such as clothing which fabric article is in direct contact with the human epidermis or (b) a therapeutic or cosmetic base adsorbed on the human epidermis each of which base includes a degradable organic amine and/or a degradable fatty acid derivative.

SUMMARY OF THE INVENTION

Our invention is directed to a fatty acid derivative and/or organic amine degradation-caused malodour-inhibiting or reducing fragrance composition containing:
(a) a mixture of 7-acetyl-1,1,2,3,4,6,7,8,8a-octahydro-1, 1,6,7-tetramethylnaphthalene 7-acetyl-1,2,3,4,5,6,7,8-octahydro-1,1,6,7-tetramethylnaphthalene and 7-acetyl-1,1,2,3,5,6,7,8,8a-octahydro-1,1,6,7-tetramethylnaphthalene (ISO-E-SUPER of International Flavors & Fragrances of New York, N.Y.);
(b) 3,7-dimethyl-3-octanol (also hereinafter referred to as tetrahydrolinalool); and
(c) 3,7-dimethyl-1,6-nonadien-3-ol (also hereinafter referred to as ethyl linalool)

and, including, optionally:
(d) n-hexyl salicylate,
(e) benzyl salicylate,
(f) a high cis isomer mixture of methyl(3'-oxo-2'-n-pentylcyclopentanyl)acetate ("high cis-methyldihyrojasmonate" or HEDIONE of Firmenich, Inc. of Plainsboro, N.J.); and/or
(g) 4-(1',1'-dimethylethyl)-α methyl benzene propanal (LILIAL of the Givaudan-Roure Corporation of Clifton, N.J.)

in synergistic combination with the malodour-inhibiting substituted t-butyl phenolic compound-containing composition which is a synergistic mixture of 2,6-di-t-butyl-4-methyl phenol (also herein referred to as BHT as well as "butylated hydroxytoluene") and pentaerythritol tetrakis(3-

(3,5-di-t-butyl-4-hydroxyphenyl) propionate) (also herein referred to as TINOGARD, Ciba Specialty Chemical Corporation of Tarrytown, N.Y.). Our invention is also directed to a process for inhibiting or reducing a malodour formed as a result of fatty acid derivative degradation and/or organic amine degradation taking place in (a) a fabric article having absorbed therein or adsorbed thereon a fabric care base, e.g. an anti-wrinkle base or an anti-static base containing one or more fatty acid derivatives and/or one or more amine derivatives or (b) the human epidermis having adsorbed thereon a cosmetic base containing one or more fatty acid derivatives and/or one or more amine derivatives, by treating the base-bearing fabric article or base-bearing human epidermis with the synergistic mixture of the t-butyl phenolic compounds: 2,6-di-t-butyl-4-methyl phenol and pentaerythritol tetrakis(3-(3,5-di-t-butyl-4-hydroxyphenyl)propionate). When carrying out the aforementioned process, the mixture of phenolic compounds may also include at least one of the aforementioned fragrance components of the malodour-reducing or inhibiting fragrance composition.

DETAILED DESCRIPTION OF THE INVENTION

Our invention provides the enablement of the inhibition and reduction of malodours which are generated as a result of fatty acid derivative and/or organic amine degradation taking place (a) on a fabric article such as clothing which fabric article is in direct contact with the human epidermis, where the fabric article has absorbed therein or adsorbed thereon a base, e.g. an anti-static base or an anti-wrinkle base which base includes a degradable organic amine and/or a degradable fatty acid derivative or (b) on the human epidermis, where the epidermis has adsorbed thereon a therapeutic or cosmetic base which base includes a degradable organic amine and/or a degradable fatty acid derivative. In addition, our invention provides the unexpected advantageous employment of the synergistic mixture of the t-butyl-substituted phenolic compounds, 2,6-di-t-butyl-4-methyl phenol and pentaerythritol tetrakis(3-(3,5-di-t-butyl-4-hydroxyphenyl)propionate) taken as a combination alone or taken further together with one or more malodour-inhibiting fragrances for inhibiting or reducing a malodour which is generated as a result of fatty acid derivative and/or organic amine degradation taking place in (a) a fabric care base absorbed in or adsorbed on a fabric article such as clothing which fabric article is in direct contact with the human epidermis or (b) a therapeutic or cosmetic base adsorbed on the human epidermis each of which bases includes a degradable organic amine and/or a degradable fatty acid derivative. The aforementioned malodour-inhibiting fragrance compositions useful in the practice of our contain:

(a) a mixture of 7-acetyl-1,1,2,3,4,6,7,8,8a-octahydro-1, 1,6,7-tetramethylnaphthalene 7-acetyl-1,2,3,4,5,6,7,8-octahydro-1,1,6,7-tetramethylnaphthalene and 7-acetyl-1,1,2,3,5,6,7,8,8a-octahydro-1,1,6,7-tetramethylnaphthalene (ISO-E-SUPER, of International Flavors & Fragrances of New York, N.Y.);

(b) 3,7-dimethyl-3-octanol (also herein referred to as tetrahydrolinalool); and (c) 3,7-dimethyl-1,6-nonadien-3-ol (also herein referred to as ethyl linalool)

and, including, optionally, (d) n-hexyl salicylate, (e) benzyl salicylate, (f) a high cis isomer mixture of methyl(3'-oxo-2'-n-pentylcyclopentanyl)acetate ("high cis-methyldihyrojasmonate" or HEDIONE, of Firmenich, Inc. of Plainsboro, N.J.); and/or (g) 4-(1',1'-dimethylethyl)-α methyl benzene propanal LILIAL of the Givaudan-Roure Corporation of Clifton, N.J.)

Preferably, the malodour-inhibiting or reducing fragrance composition useful in the practice of our invention in conjunction with the t-butyl phenolic compound composition of our invention comprises:

(a) from about 1 up to about 10% by weight of n-hexyl salicylate;

(b) from about 1 up to about 10% by weight of a mixture of 7-acetyl-1,1,2,3,4,6,7,8,8a-octahydro-1,1,6,7-tetramethylnaphthalene 7-acetyl-1,2,3,4,5,6,7,8-octahydro-1,1,6,7-tetramethylnaphthalene and 7-acetyl-1,1,2,3,5,6,7,8,8a-octahydro-1,1,6,7-tetramethylnaphthalene;

(c) from about 2 up to about 10% by weight of benzyl salicylate;

(d) from about 2 up to about 20% by weight of 3,7-dimethyl-3-octanol;

(e) from about 3 up to about 20% by weight of 3,7-dimethyl-1,6-nonadien-3-ol;

(f) from about 7 up to about 30% by weight of a high cis isomer mixture of methyl(3'-oxo-2'-n-pentylcyclopentanyl)acetate; and (g) from about 7 up to about 30% by weight of 4-(1',1'-dimethylethyl)-α methyl benzene propanal.

The use of t-butyl-substituted phenolics such as BHT and TINOGARD as stabilizers and anti-oxidants is disclosed in U.S. Pat. Nos. 5,158,992 and 5,910,52.

The term organic amine is herein intend to mean any organic amine which is biodegradable, including but not limited to monoalkyl amines, dialkyl amines, trialkyl amines, quaternary ammonium salts and polyamines, including for example dimethyl di(hydrogenated tallow alkyl)ammonium chloride. The term fatty acid derivative is herein intended to any fatty acid derivative which is biodegradable, for example free fatty acids, including lauryl, palmitic and stearic acid, and fatty acid esters and mono, di and triglycerides, as well as homopolymers and other biodegradable polymers of unsaturated fatty acids.

More specifically, our invention covers a process for inhibiting a malodour formed as a result of fatty acid derivative and/or organic amine derivative degradation, including biodegradation taking place (a) in a fabric article having absorbed therein or adsorbed thereon a fabric care base containing one or more fatty acid derivatives and/or one or more organic amine derivatives or (b) on the human epidermis having adsorbed thereon a therapeutic or cosmetic base containing one or more fatty acid derivatives and/or one or more organic amines comprising the step of treating said base-bearing fabric article or human epidermis with a malodour-inhibiting quantity and concentration of a synergistic malodour-inhibiting or reducing substituted phenolic compound-containing composition comprising 2,6-di-t-butyl-4-methyl phenol and pentaerythritol tetrakis(3-(3,5-di-t-butyl-4-hydroxyphenyl)propionate) with the weight ratio of 2,6-di-t-butyl-4-methyl phenol:pentaerythritol tetrakis(3-(3, 5-di-t-butyl-4-hydroxyphenyl)propionate) being from about 0.01:1 up to about 5:1, over a malodour-inhibiting period of time of from about 0.5 hours up to about 6 months.

Preferably, the weight ratio of 2,6-di-t-butyl-4-methyl phenol:pentaerythritol tetrakis(3-(3,5-di-t-butyl-4-hydroxyphenyl)propionate) is from about 2:1 up to about 4:1.

Application of the malodour-inhibiting or reducing compositions of our invention can be carried out by means of aerosol treatment of the human epidermis or fabric articles or by application of a non-aerosol liquid spray from a spray dispenser such as a manually-activated trigger-spray dispenser or non-manually operated spray dispenser or by application of the composition by means of manual liquid coating of the human epidermis or fabric article or by means of immersion of the fabric article in the composition of our invention. When application is carried out by means of the use of a spray dispenser, the process may be carried out as disclosed by U.S. Pat. No. 6,528,013. When application is carried via use of aerosol techniques, the aerosol application process may be carried out as taught in U.S. Pat. No. 6,555,092.

It is preferable that the malodour-inhibiting or reducing composition useful in the practice of our invention contains a compatible carrier, preferably water or, in the case of aerosols, a compatible aerosol spray propellant such as trichloromonofluoromethane and dichlorodifluoromethane (respectively, FREON 11 and FREON 12, E.I. Du Pont de Nemours & Co. of Wilmington, Del.), dimethyl ether, n-propane, isobutene or the like and a solvent such as ethyl alcohol, isopropyl alcohol, benzyl alcohol, propylene glycol monomethyl ether, propylene glycol monoethyl ether and ethylene glycol monophenyl ether as disclosed in U.S. Pat. No. 6,555,092. When the malodour inhibiting or reducing phenolic compound-containing composition contains a compatible carrier, or an aerosol propellant and/or an additional fragrance material, it is preferred that the 6-di-t-butyl-4-methyl phenol-pentaerythritol tetrakis(3-(3,5-di-t-butyl-4-hydroxyphenyl)propionate) mixture be present in an amount of from about 3% up to about 6% by weight of said malodour-inhibiting composition with the remainder of the composition being carrier, aerosol propellant, aerosol solvent and/or fragrance substance.

When the malodour-inhibiting or reducing composition of our invention is applied to a fabric article in accordance with the process of our invention, it is preferred that the malodour-inhibiting or reducing substituted phenolic compound-containing composition is applied to a fabric article in an amount of from about 0.1 up to about 10 weight % of the fabric article.

The fabric care bases which contain degradable organic amines and/or fatty acid derivatives with which the process and composition of our invention are useful include anti-wrinkle bases and anti-static bases. Anti-wrinkle bases contain, for example, homopolymers of long chain $C_8$–$C_{18}$ unsaturated carboxylic acids and quaternary ammonium compounds such as polyaminopropyl biguanide as disclosed in U.S. Pat. No. 6,528,013. Anti-static bases contain those disclosed in U.S. Pat. Nos. 3,676,199, 3,634,947, 6,436,894, 6,235,705 and 6,133,226, dialkyl ditallow ammonium halide such as dimethyl ditallow ammonium chloride, laurylalkanolamides, tertiary ethoxylated cocoamines and tallow amines such as ARMOSTAT 300 and ARMOSTAT 400, Akzo Nobel Chemicals,B. V. of Amersfoort, Netherlands, and acyloxyalkyl quaternary ammonium compositions as set forth in Published U.S. patent application Ser. No. 2003/0069164.

Skin care bases which contain degradable organic amines and/or fatty acid derivatives with which the process and composition of our invention are useful include cosmetic and therapeutic compositions. Cosmetic compositions which contain fatty acid derivatives are set forth in U.S. Pat. No. 6,558,680 and published Application for U.S. Patent 2001/0031280, such as polyvinyl laurate and octyl isostearate. Therapeutic compositions for the human epidermis are disclosed in U.S. Pat. Nos. 6,514,489 and 6,558,680.

This invention will be explained further by a consideration of the following Examples which are given solely for the purpose of illustration and are not to be construed as limitations of the present invention since many variations thereof are possible without departing from the scope or spirit of the invention. All issued U.S. Patents and patent applications disclosed throughout this specification are hereby incorporated by reference as if set forth in their entirety. The compositions of the following Examples A and B are used in Examples I, II and III, infra.

EXAMPLE A

The following fragrance compositions are prepared:

| | Parts by Weight | |
|---|---|---|
| Ingredient | A-1 | A-2 |
| n-hexyl salicylate | 10 | |
| ISO-E-SUPER | 10 | 30 |
| benzyl salicylate | 10 | |
| tetrahydrolinalool | 20 | 35 |
| ethyl linalool | 15 | 35 |
| high cis-methyl dihydrojasmonate | 20 | |
| LILIAL | 15 | |

EXAMPLE B

The following t-butyl phenolic compound compositions are prepared:

| | Parts by Weight | |
|---|---|---|
| Ingredient | B-1 | B-2 |
| 2,6-di-t-butyl-4-methyl phenol (BHT) | 60 | 80 |
| pentaerythritol tetrakis(3-(3,5-di-t-butyl-4-hydroxyphenyl) propionate) (TINOGARD TT) | 30 | 20 |

EXAMPLE I

Anti-Wrinkle/Anti-Static Composition and Process for Applying Same to Fabric Articles The following mixtures are prepared:

| | Parts by Weight | | | | |
|---|---|---|---|---|---|
| Ingredient | I(a) | I(b) | I(c) | I(d) | I(e) |
| Anti-Wrinkle Composition of Example Va of U.S. Pat. No. 6,528,013 also containing 1.5 wt. % of the anti-static agent, triethanol amine-hard tallow based ester quat 10 prepared according to Example 5 of Published U.S. Patent application 2003/0069164 | 100 | 95 | 95 | 90 | 90 |
| Perfume Composition of | | | | | 6.5 |

-continued

| Ingredient | I(a) | I(b) | I(c) | I(d) | I(e) |
|---|---|---|---|---|---|
| Perfume Composition of Example A-1 | | | | 6.5 | |
| Perfume Composition of Example A-2 | | | | | 6.5 |
| t-Butyl phenolic compound composition of Example B-1 | | 5.0 | | 3.5 | |
| t-Butyl phenolic compound composition of Example B-2 | | | 5.0 | | 3.5 |

Each of the compositions of Examples I(a), I(b), I(c), I(d) and I(e) is sprayed onto five cotton/polyester pull-over shirts using a Calmar TS 1300 trigger sprayer available from Calmar, Inc. of City of Industry, Calif. Each of the shirts is worn by five individual male wearers each in the age group: 18–20 years, intermittently, over a period of three weeks for periods of 12 hours per day. Immediately after the three week periods, each of the shirts is tested for residual malodour. Malodour evolved from the shirts treated with compositions of Examples I(b), I(c), I(d) and I(e) is significantly less than the malodour evolved from the shirts treated with the compositions of Example I(a).

EXAMPLE II

Anti-Static Aerosol Treatment of Suits

The following mixtures are prepared:

| Ingredient | II(a) | II(b) | II(c) | II(d) | II(e) |
|---|---|---|---|---|---|
| Anti-Static Composition of Example I of U.S. Pat. No. 3,634,947 containing 30 weight % ethanol, 55 wt. % of the anti-static agent, distearyl dimethyl ammonium chloride and 15% water | 100 | 60 | 60 | 60 | 60 |
| Perfume Composition of Example A-1 | | | | 15 | |
| Perfume Composition of Example A-2 | | | | | 15 |
| t-Butyl phenolic compound composition of Example B-1 | | 40 | | 25 | |
| t-Butyl phenolic compound composition of Example B-2 | | | 40 | | 25 |

15 Grams of each of the compositions of Examples II(a), II(b), II(c),II(d) and II(e) is inserted, respectively, into five 250 milliliter high pressure aerosol containers. After attaching aerosol valves to the aerosol containers, 135 grams of a 50:50 mixture of propylene glycol monomethyl ether solvent and dimethyl ether propellant is packed into each of the aerosol containers. After shaking the contents of each of the containers, each composition is sprayed onto a suit jacket. Each suit jacket is stored for 24 hours, and worn by a male person in the age group, 25–35 years for 10 periods of 8 hours each over a five week period. Immediately after the five week periods, each of the suit jackets is tested for residual malodour. Malodour evolved from the suit jackets treated with compositions of Examples II(b), II(c), II(d) and II(e) is significantly less than the malodour evolved from the jackets treated with the compositions of Example II(a).

EXAMPLE III

Skin Care Compositions

The following skin care compositions are prepared:

| Ingredient | III(a) | III(b) | III(c) | III(d) | III(e) |
|---|---|---|---|---|---|
| Composition of Example 5 of U.S. Pat. No. 6,558,680 containing 1.2% by wt. of stearic/palmitic acid, 1.2% by wt. PEG-100 stearate and 3.6% by wt. of glyceryl stearate; but not containing any perfume or preservatives | 100 | 95 | 95 | 90 | 90 |
| Perfume Composition of Example A-1 | | | | 6.5 | |
| Perfume Composition of Example A-2 | | | | | 6.5 |
| t-Butyl phenolic compound composition of Example B-1 | | 5.0 | | 3.5 | |
| t-Butyl phenolic compound composition of Example B-2 | | | 5.0 | | 3.5 |

Each of the compositions of Examples III(a), III(b), III(c),III(d) and III(e) is applied to the right forearm of a female subject in the age group, 21–23; and the residue is permitted to remain for 24 hours. Immediately after the 24 hour period, malodour evolved from each of the skin areas treated with compositions of Examples III(b), III(c), III(d) and III(e) is significantly less than the malodour evolved from the skin area treated with the composition of Example III(a).

What is claimed is:

1. A process for inhibiting or reducing a malodour formed as a result of fatty acid derivative and/or organic amine derivative-biodegradation wherein the fatty acid derivative and/or organic amine derivative biodegradation are selected from the group consisting of lauryl acid, palmitic acid, stearic acid, fatty acid esters, monoglycerides, diglycerides, triglycerides, monoalkyl amines, dialkyl amines, trialkyl amines, dimethyl di(hydrogenated tallow alkyl)ammonium chloride and mixtures thereof taking place (a) in a fabric care base absorbed in or adsorbed on a fabric article containing one or more fatty acid derivatives and/or one or more organic amine derivatives or (b) in a therapeutic or cosmetic base adsorbed on the human epidermis comprising the step of treating said fabric article or said human epidermis with a malodour-inhibiting quantity and concentration of a malodour-inhibiting or reducing substituted phenolic compound-containing composition consisting of 2,6-di-t-butyl-4-methyl phenol and pentaerythritol tetrakis(3-(3,5-di-t-butyl-4-hydroxyphenyl) propionate) with the weight ratio of 2,6-di-t-butyl-4-methyl phenol:pentaerythritol tetrakis(3-(3,5-di-t-butyl-4-hydroxyphenyl)propionate) being from about 2:1 up to about 4:1, over a malodour-inhibiting or reducing period of time.

2. The process of claim 1 wherein the malodour-inhibiting or reducing substituted phenolic compound-containing composition is applied to a fabric article in an amount of from about 0.1 up to about 10 weight % of the fabric article.

3. The process of claim 1 wherein the step of treating the fabric article or human epidermis with the malodour-inhibiting or reducing composition comprises spraying the malodour-inhibiting or reducing composition onto the surface of the fabric article or human epidermis as an aerosol.

* * * * *